US009376656B2

(12) United States Patent
Bartilson

(10) Patent No.: US 9,376,656 B2
(45) Date of Patent: Jun. 28, 2016

(54) PHOTOBIOREACTOR SYSTEM AND METHOD FOR THE GROWTH OF ALGAE FOR BIOFUELS AND RELATED PRODUCTS

(76) Inventor: Brad W. Bartilson, Columbia, NJ (US)

( * ) Notice: Subject to any disclaimer, the term of this patent is extended or adjusted under 35 U.S.C. 154(b) by 371 days.

(21) Appl. No.: 12/414,149

(22) Filed: Mar. 30, 2009

(65) Prior Publication Data

US 2010/0248333 A1   Sep. 30, 2010

(51) Int. Cl.
| | | |
|---|---|---|
| C12M 1/00 | (2006.01) | |
| C12M 1/12 | (2006.01) | |
| C12M 3/00 | (2006.01) | |

(52) U.S. Cl.
CPC ............ *C12M 31/08* (2013.01); *C12M 21/02* (2013.01); *C12M 23/06* (2013.01); *C12M 23/26* (2013.01); *C12M 23/38* (2013.01); *C12M 23/44* (2013.01); *C12M 23/50* (2013.01); *C12M 27/20* (2013.01); *C12M 29/22* (2013.01)

(58) Field of Classification Search
CPC ...... C12M 21/02; C12M 23/06; C12M 23/26; C12M 23/38; C12M 31/08; C12M 23/50; C12M 27/20; C12M 29/22; C12M 23/44
USPC ............................................ 435/257.1, 292.1
See application file for complete search history.

(56) References Cited

U.S. PATENT DOCUMENTS

| 1,643,273 | A | | 9/1927 | Imhoff | |
| 4,868,123 | A | * | 9/1989 | Berson et al. | 435/286.6 |
| 2005/0176131 | A1 | * | 8/2005 | Flickinger et al. | 435/243 |
| 2007/0048848 | A1 | | 3/2007 | Sears | |
| 2007/0289206 | A1 | | 12/2007 | Kertz | |
| 2008/0009055 | A1 | | 1/2008 | Lewnard | |
| 2008/0160591 | A1 | | 7/2008 | Willson et al. | |
| 2008/0178739 | A1 | | 7/2008 | Lewnard et al. | |
| 2008/0220515 | A1 | | 9/2008 | McCall | |

(Continued)

FOREIGN PATENT DOCUMENTS

| EP | 0 310 522 A1 | 4/1989 |
| GB | 2 235 210 A | 2/1991 |

(Continued)

OTHER PUBLICATIONS

Barbosa, "Microalgal Photobioreactors: Scale-Up and Optimization", PhD thesis, Wageningen University, Sep. 12, 2003, 1-168.

(Continued)

*Primary Examiner* — Gautam Prakash
(74) *Attorney, Agent, or Firm* — Baker Hostetler LLP

(57) ABSTRACT

A photobioreactor includes an upper layer of transparent film and a lower layer of film wherein the upper layer and lower layer are attached to each other along the perimeter to form a sealed structure, the upper layer and lower layer also attached to form pathways comprising independent channels within the confines of the outer perimeter, a first manifold and second manifold on opposite ends of the parallel channels within the sealed structure wherein a first portion of the first manifold is in fluid communication with each of an inlet of a first subset of the channels and a second portion of the first manifold is in fluid communication with each of an outlet of a second subset of the channels and wherein the second manifold is in fluid communications with the distal end of the parallel channels plumbing apparatus comprising a degas vessel in fluid communication with the first manifold; and wherein the structure is substantially horizontal in operation.

19 Claims, 16 Drawing Sheets

(56) References Cited

U.S. PATENT DOCUMENTS

| | | |
|---|---|---|
| 2008/0268302 A1 | 10/2008 | McCall |
| 2008/0274494 A1 | 11/2008 | Kertz |
| 2008/0286851 A1 | 11/2008 | Whitton |
| 2008/0299643 A1 | 12/2008 | Howard et al. |
| 2008/0311649 A1 | 12/2008 | Cloud et al. |
| 2009/0011492 A1 | 1/2009 | Berzin |
| 2009/0291485 A1* | 11/2009 | Shigematsu et al. ....... 435/257.1 |
| 2011/0151507 A1 | 6/2011 | Van Walsem et al. |
| 2012/0021498 A1 | 1/2012 | Muller-Feuga |

FOREIGN PATENT DOCUMENTS

| | | |
|---|---|---|
| GB | 2 339 763 A | 2/2000 |
| WO | WO 2008/151373 | 12/2008 |
| WO | WO 2010/117720 | 10/2010 |

OTHER PUBLICATIONS

Christi, "Biodiesel from Microalgae", Biotechnology Advances, Feb. 13, 2007, 25, 294-306.

Dimitrov, "Greenfuel Technologies: A Case Study for Industrial Photosynthetic Energy Capture", GreenFuel Technologies, Mar. 2007, Brisbane Australia, 1-30.

Ono et al., "Design Parameters of Solar Concentrating Systems for $CO_2$ Mitigating Algal Photobioreactor", The University of Arizona, Energy, 6$^{th}$ International Conference on Greenhouse Gas Control Technologies, Jul.-Aug. 2004, 29(9-10), 1651-1657—(Abstract).

\* cited by examiner

| Chan. Width (in) | Broth Conc. (g/L) | # Chan. (#) | Press. Drop (psi) | Req'd Wall thick. (mil) | Total Flow Rate (gpm) | Pump Power (kW) | Degass Vessel Size (gal's) | Yearly Power (kW-hr) | kW-hr /gal (kW-hr) | Pump'g Cost (\$/gal) |
|---|---|---|---|---|---|---|---|---|---|---|
| 80 | 0.78 | 8 | 11558 | 6.1 | 0.76 | 7495 | 26.5 | 3122 | 93072 | 3.00 | 0.18 |
| 80 | 0.86 | 6 | 10362 | 3.5 | 0.54 | 8337 | 17.0 | 4309 | 59601 | 1.85 | 0.11 |
| 80 | 1.02 | 4 | 8829 | 1.6 | 0.34 | 9629 | 9.2 | 6745 | 32234 | 0.96 | 0.06 |
| 40 | 0.78 | 8 | 23116 | 4.3 | 0.54 | 14990 | 37.5 | 3122 | 131614 | 4.24 | 0.25 |
| 40 | 1.02 | 4 | 17658 | 1.3 | 0.27 | 19258 | 14.2 | 6745 | 49741 | 1.48 | 0.09 |
| 20 | 0.78 | 8 | 46231 | 3.4 | 0.43 | 29979 | 59.5 | 3122 | 208699 | 6.72 | 0.40 |
| 20 | 0.86 | 6 | 41447 | 2.1 | 0.33 | 33349 | 40.8 | 4309 | 143144 | 4.45 | 0.26 |
| 20 | 1.02 | 4 | 35317 | 1.1 | 0.23 | 38515 | 24.1 | 6745 | 84754 | 2.53 | 0.15 |
| 10 | 0.78 | 8 | 92463 | 3.0 | 0.37 | 59958 | 103.4 | 3122 | 362868 | 11.69 | 0.69 |
| 10 | 1.02 | 4 | 70633 | 1.0 | 0.21 | 77030 | 44.1 | 6745 | 154781 | 4.62 | 0.27 |

Figure 16

PHOTOBIOREACTOR SYSTEM AND METHOD FOR THE GROWTH OF ALGAE FOR BIOFUELS AND RELATED PRODUCTS

TECHNICAL FIELD

This application is directed generally to the fields of energy, biofuels, and biochemistry, and more specifically to a low cost technique for a large area photobioreactor, optimized for algae growth.

BACKGROUND

Primary requisites for algal growth systems are photon acceptance, water, trace nutrients, and a carbon source. Carbon dioxide is a common choice for the carbon source as it is an environmentally-destructive gas (aka "greenhouse gas") which can be extracted from the stack emissions of electrical generating facilities. With proper control of the requisite ingredients, algae can be grown and harvested continuously during sunlight hours.

There are two basic types of algal growth systems-open and closed systems. Open systems (aka "open ponds" or "open raceway" systems) consist of an enclosed pond in which the algae are fed nutrients, $CO_2$ and are directly exposed to sunlight to permit photosynthesis. In the open raceway configuration the pond is an oval shape with a central divider and paddle wheel to induce continuous flow around this oval "race track". U.S. Pat. No. 1,643,273 teaches the basic concept of continuous loop raceway for aquaculture.

The Department of Energy demonstrated the production of biodiesel from algae in its "Aquatic Species Program" in operation from 1979-1996. This program, while forefronting algae biofuels production, found its process non-competitive with fossil fuels, with issues of species invasion (the directed algae were quickly overcome by indigenous algae species of a lower lipid content), evaporation, and high processing costs. Open ponds have direct exposure to all environmental events. Additionally, the fixed nature of open pond design prevents change for future design enhancements and/or reconfiguration for plant layout modification. The construction of such systems typically exceeds $100/m2. On a ten year basis, the amortized yearly cost of open ponds is $10/m2, even ignoring the time value of money. Operating costs have recently been reported as low as $30/m2, yet this still renders oil cost over $10/gallon. The economics render the systems commercially impractical.

Covers have recently been added to open raceway systems, e.g. US Patent Applications Nos. 20080178739 and 2008299643. This addition lessens the environmental effects, and can reduce evaporation and improve the thermal control of the system. The cover however adds to the cost basis. And the reduced sunlight delivered to the pond surface will further erode photosynthetic performance. Yusuf Christi in "Biodiesel for microalgae" a research paper in Biotechnology Advances 25 (2007) reports findings of open ponds without covers exhibit 37% lower biomass and oil yield relative to closed systems or "photobioreactors".

First generation closed systems or "photobioreactors" utilized transparent tubes made of rigid plastic (e.g. acrylic) through which the algal broth is pumped. The closed system provides isolation from environmental events and infiltration from other species. Greater process control is achieved, as evidenced by the higher productivity. This design is somewhat more available to design change and reconfiguration. US Patent #20090011492 teaches the use of large diameter acrylic tubes held at a highly inclined angle and having internal recirculation paths within the tubes.

While averting or reducing the drawbacks of open pond systems, the acrylic tube photobioreactors have been shown to be prohibitively expensive—characteristic costs are $190/m2, thus rendering this approach economically unsustainable. Further, research has shown that in dense broth processes (process efficiency is generally improved with higher broth density) light does not penetrate far into the broth within the tube, leaving a large dark zone.

Others have developed light-pipe systems to increase the volumetric efficiency of photobioreactors. McCall in patent applications 20080268302 and 20080220515 teach the use of parallel, edge transmitting devices mounted within the cultivation zone, to increase the depth of the photosynthetic activity. Wilson in patent application 20080160591 describes transparent panels having extended, light transmissive surfaces attached to the light impinged surface thereby extending the depth of light penetration. An alternative approach, wherein the light is gathered in solar concentrating systems and then delivered by light emitting fibers into the algae broth is described by Ono and Cuello in Design Parameters of Solar Concentrating Systems for CO2 Mitigating Algal Photobioreactor" The University of Arizona, "Energy" 29: 1651-1657. Therein the light transfer efficiency is stated to now be improved to 45%.

More recently, transparent film has been used in photobioreactors to achieve lower cost. Kerz in patent application 20080274494 teaches the construction of vertically-held sheets of plastic joined in such manner as to create horizontal flow channels which cascade downward in serial fashion, top-to-bottom as driven by gravity. Constructed in this manner, significant surface area can be developed per unit of floor area. The sheets are suspended and mechanically-rotated within a greenhouse enclosure. While this approach leverages a lower cost photobioreactor material, the added costs of the machinery and the surrounding greenhouse greatly challenge profitable operation.

Alternatively, Sears in patent application 20070048848 teaches the use of large and long transparent bags configured in dual-arrangement, having CO2 injected into the algae broth at one end connecting the two bags, and water/nutrients and harvesting occurring at the opposite connection end. Motion is imparted to the broth via a weighted roller mechanical drive over the bag, thereby squeezing the broth down the bag, in peristaltic manner. The arrangement is then similar to an open-raceway system, yet being enclosed in the bag. Therein, an elaborate containment and track support structure is displayed, impacting the design flexibility and challenging the cost model.

Cloud, in patent application 20080311649 displays a parallel arrangement of 6 inch diameter tubes made of transparent film, The separate tubes are pressured by the pumped algae broth, with no internal means of interconnection along the pathway, nor a novel means of end connection to avert substantial fitting cost. The large size of the tube induces large, unproductive dark zones.

What is lacking in current approaches is a financial-based approach to the design. The material selections, inefficient use the material in orientation and/or geometry, process equipment, and process configurations of current approaches neglect the use of profitability-driven parameters, thus precluding an economically-viable solution. Survivability through environmental events, such as a hailstorm, must also be a part of the design in order to support a viable financial model. Flexibility, that is, the ability to alter the design without incurring expenses of such magnitude as to collapse the financial model, is also of great importance, as the surrounding technology base (algae growth characteristics, carbon and nutrient sourcing, and lipid extraction) is changing due to the infancy of the industry.

SUMMARY

In accordance with the present invention, there is a photobioreactor including an upper layer of transparent film and a lower layer of film wherein the upper layer and lower layer are attached to each other along the perimeter to form a sealed structure, the upper layer and lower layer also attached to form pathways comprising independent channels within the confines of the outer perimeter, a first manifold and second manifold on opposite ends of the parallel channels within the sealed structure wherein a first portion of the first manifold is in fluid communication with each of an inlet of a first subset of the channels and a second portion of the first manifold is in fluid communication with each of an outlet of a second subset of the channels and wherein the second manifold is in fluid communications with the distal end of the parallel channels, a plumbing apparatus comprising a degas vessel in fluid communication with the first manifold, wherein the structure is substantially horizontal in operation. The embodiments include the channels are parallel to each other; the structure being is slightly inclined at less than 30 degrees from the horizontal., the channels being of a serpentine pattern, the independent channels are parallel and have substantially similar cross-sectional areas under pressure. Additional embodiments may have a plurality of flow restrictor elements placed at the inlet to each of the independent parallel channels, a pump connected to the first manifold, a lower layer made of a transparent material, or made of material that reflects light or having the lower layer provides abrasion resistance, puncture resistance, a reflective surface, or plant growth resistance. Additionally, the photobioreactor may have a protective layer positioned above the top layer including a mesh or transparent material. The preferred embodiment may be designed with flow channels to exhibit a Reynolds number between 500 and 4000, or wherein the flow channels have a cross-sectional area of less than or equal to 6 inches in diameter or wherein the number and size of channels and channel diameter are determined by algae dependent variables of flow channel Reynolds number and field length as determined by degassing of algae or wherein the number of channels is parabolically decreasing with increasing photobiorector length. As shown in the detailed description, the photobioreactor may have a channel diameter (or equivalent diameter for non-circular cross sections) that is linearly decreasing with the broth density, and the channel count is linearly increasing with broth density and wherein the pressure drop increases linearly with reactor length and with broth density, thereby giving rise to greater photobioreactor material thickness. The photobioreactor may have a pumping rate that decreases parabolically with respect to reactor length and wherein the pumping power as determined by a product of flow rate and pressure drop is a parabolically decreasing function with respect to reactor length. The photobioreactor has a reactor length is the longest reactor length possible for the given degassing limit and use of the highest broth density. Alternatively, the protective cover is a second photobioreactor laid on top the photobioreactor wherein the channels of each photobioreactor are interdigitated such that the channels of the upper photobioreactor are positioned the seam areas of the lower photobioreactor. the second photobioreactor providing process options including alternative photosynthetic process and shading options.

BRIEF DESCRIPTION OF THE DRAWINGS

The foregoing and other aspects of the present invention will be better understood from the following detailed description with reference to the drawings.

FIG. 16 is a table summarizing the analysis for a number of variables.

DETAILED DESCRIPTION OF ILLUSTRATIVE EMBODIMENTS

Figure 1:
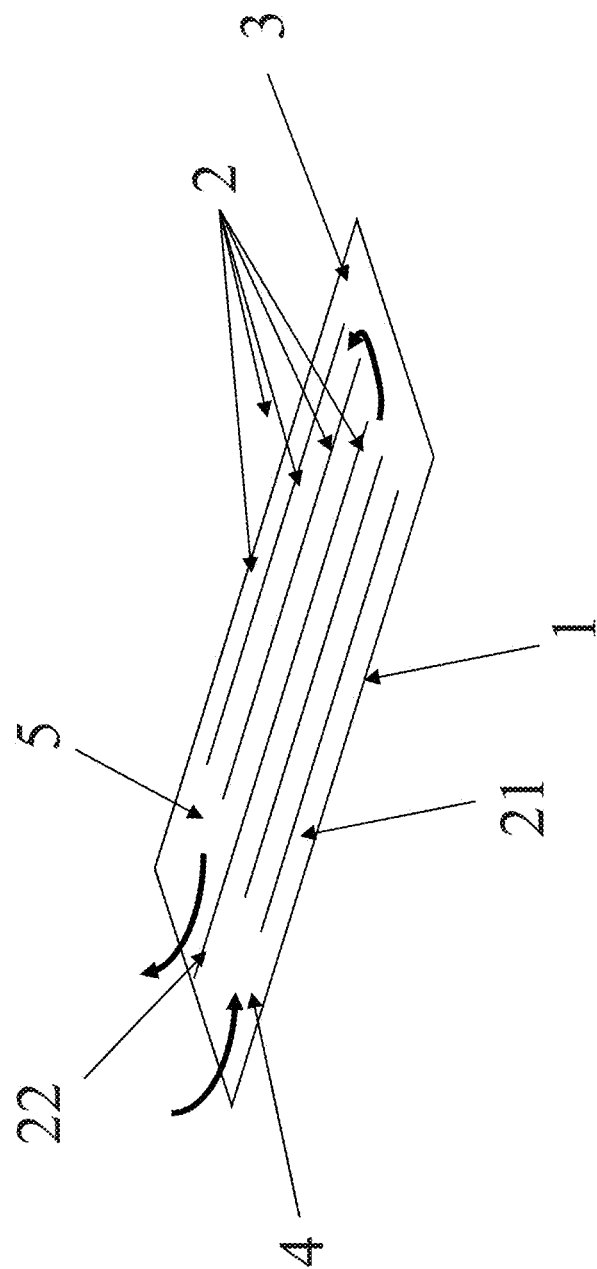
FIG. 1 is an illustration of the polyfilm photobioreactor ("PFR") constructed of in accordance with the present invention in an unpressurized state

The subject matter of the various embodiments is described with specificity to meet statutory requirements. However, the description itself is not intended to limit the scope of this patent. Rather, the inventor has contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly required. It should be understood that the explanations illustrating data or algae flows are only exemplary. The following description is illustrative and non-limiting to any one aspect.

A physics-driven cost model provides a framework for an economically-viable, and scalable, algae-biofuels system. Firstly, the present invention recognizes that sunlight, as the driving energy input to the system, places an intrinsic limit on the production per unit area. Of the impaled sunlight on the earth's surface, only those photons acting in the 400-700 nm range, known as the photosynthetically active region or "PAR", can contribute to photosynthesis. For the southwest United States, the total seasonal PAR value availed is 105 Watts per square meter according to the Department of Atmospheric and Oceanic Science University of Maryland, College Park.

Photosynthesis then places an upper bound on the use of these select photons. From the FAO (Food and Agricultural Organization), (see Maria Barbosa "Microalgae photobioreactors: Scale-up and optimization" PhD Thesis 2003) experimental data indicates that between 8 and 12 photons are required for fixation of one molecule of $CO_2$. Since the energy equivalent of one photon (700 nm) is approximately 170 kJ/E, and the change in free energy during the fixation of $CO_2$ is approximately 450 U/mol, the energy efficiency of this process for monochromatic light of a wavelength of 700 nm is estimated to be approximately 21-33%.

From this conversion efficiency, cell losses (inefficiency in transfer of energy through the cell wall, use of the energy within the cell) reduce an assumed converted energy average from 27% to 15% of the initial energy. In the case of a photobioreactor, transmission, reflectance, shading and fouling losses impart losses that reduce the feasible system efficiency to about 10% (see, "GreenFuel Technologies: A Case Study for Industrial Photosynthetic Energy Capture" Krassen Dimitrov, Ph.D. March, 2007 Brisbane, Australia). Additionally Christi in a research paper in Biotechnology Advances 25 ("Biodiesel from microalgae") (2007), pages 294-306 confirms this with an 8% value displayed in a tubular photobioreactor system. Note that while open systems can avert the wall losses of photobioreactors, the lessened controls, evaporation and reduced uniformity of light dispersion, ultimately renders them less efficient photobioreactors.

Applying the above formulation (using 10% conversion efficiency and a PAR value of 105 $W/m^2$) a reasonable yearly production limit of biodiesel (120 GJ/gallon) is 2.67 gallons per square meter. At the market pricing as of February 2009, revenue is just $6 per square meter. Rudimentary financial modeling of end-end system, incorporating cost of land, feedstock, growth system processing, midstream and downstream processing, marketing, distribution and taxes, easily projects a limit of $15 per square meter on installed growth system cost for a commercially economically viable system.

Secondly, the design formulation of the current invention recognizes the limited return on materials expended, in the vertical orientation as is currently taught by others in the art. In perfect transmission, a largely flat, horizontal surface captures the significant portion of the available photons (either directly or secondarily via reflectance), and importantly, does not shade any other surface area. While additional of large vertical surfaces can offer secondary transmission into the algae, the return-on-investment, given the efficiency and material cost, is not attractive.

Figure 2:
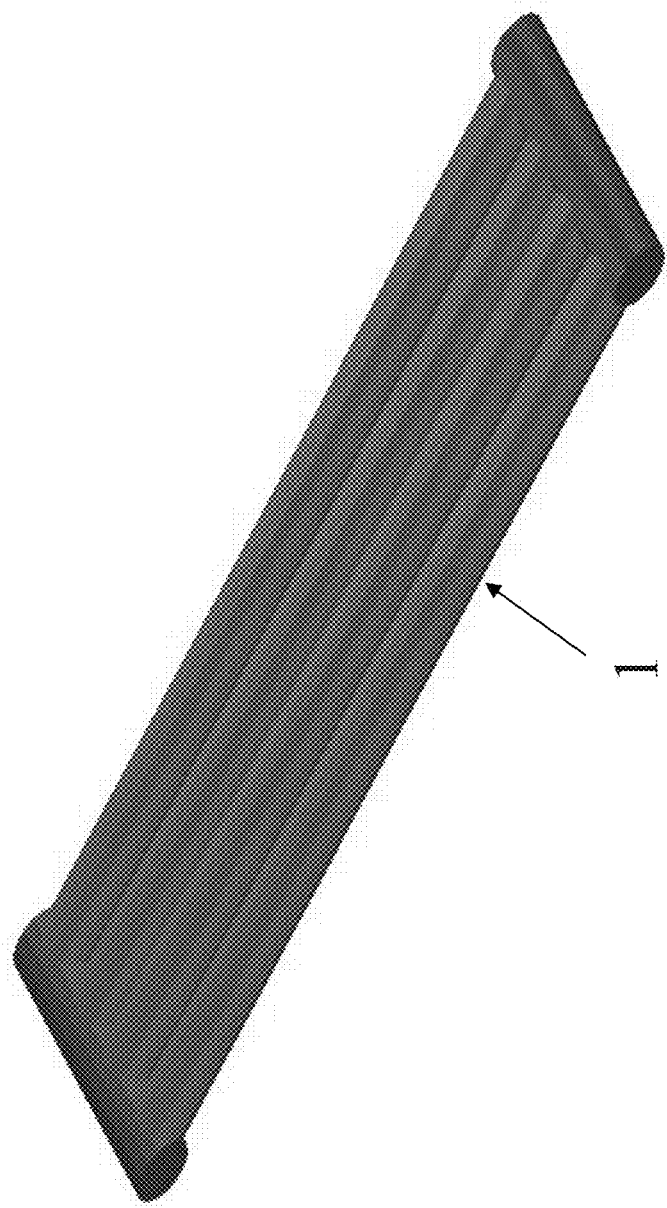
FIG. 2 is an illustration of the PFR of FIG. 1 n the pressurized (working) state.
Figure 3:
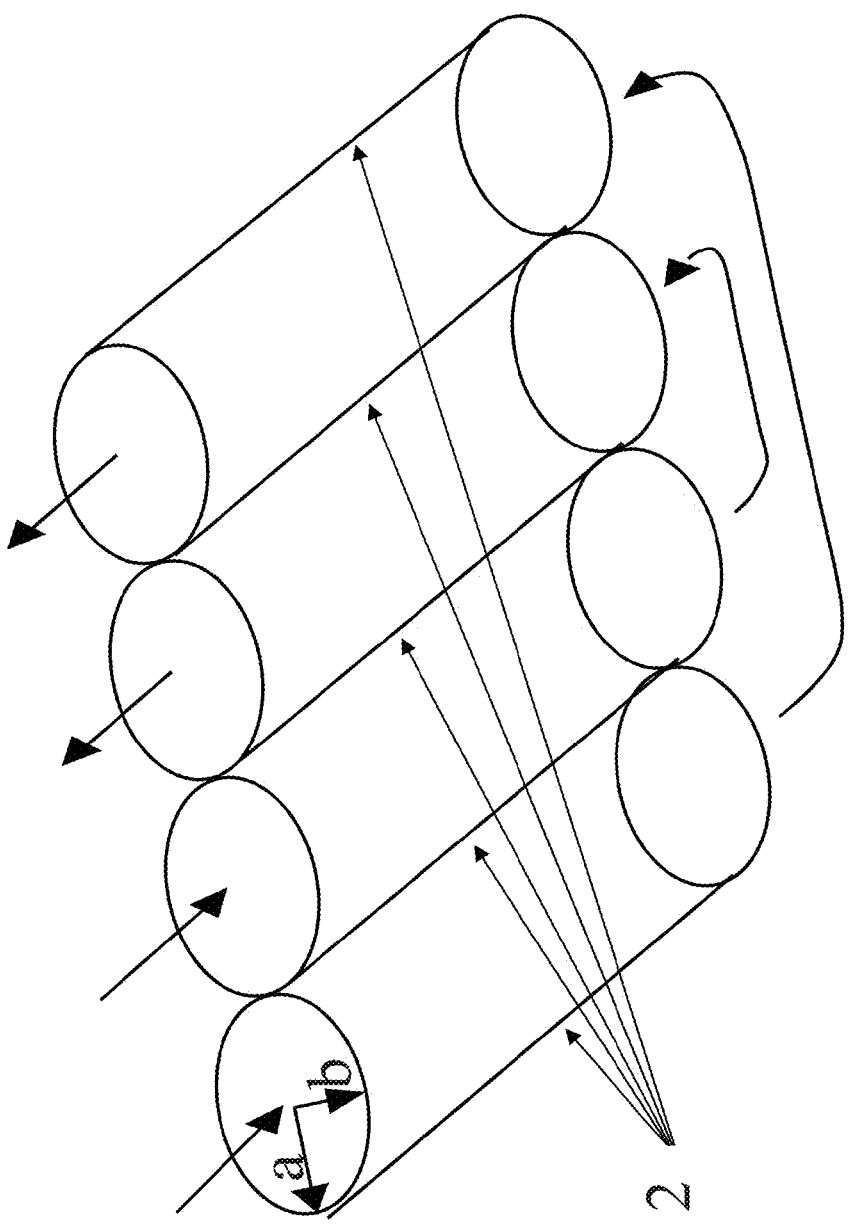
FIG. 3 illustrates the elliptical form of the PFR flow channels.

In the present invention, an upper and lower sheet of film (upper layer being transparent) may be joined in such manner as to create flow channels between the sheets. With reference to FIG. 1, the photobioreactor (or "PFR" for "poly-film reactor" as used interchangeably herein) 1 is shown with seams 2 joining the sheets to form flow channels 21 therebetween, and a divider 22 between opposing flow sections of the PFR 1. The flow channels 21 may be combined at manifolds 4 and 5 where the flow enters and exits the PFR 1. The manifolds may also serve to return the flow, without the use of connectors to the same end of the PFR 1 as shown in FIG. 1. Once pressurized by the working fluid (algae "broth") the flow channels and the manifolds become inflated to the working geometry as shown in FIG. 2. Due to the slight asymmetry of the joint geometry, the flow channels my take on a slightly elliptical shape as shown in FIG. 3.

Polyethylene film presents one example for the construction material, being commercially-available with UV and IR blocking agents (a.k.a. "greenhouse film") and whose cost is within system target levels for economic viability (currently two layers 6 mil thick amount to less than $3 per square meter).

Figure 4:
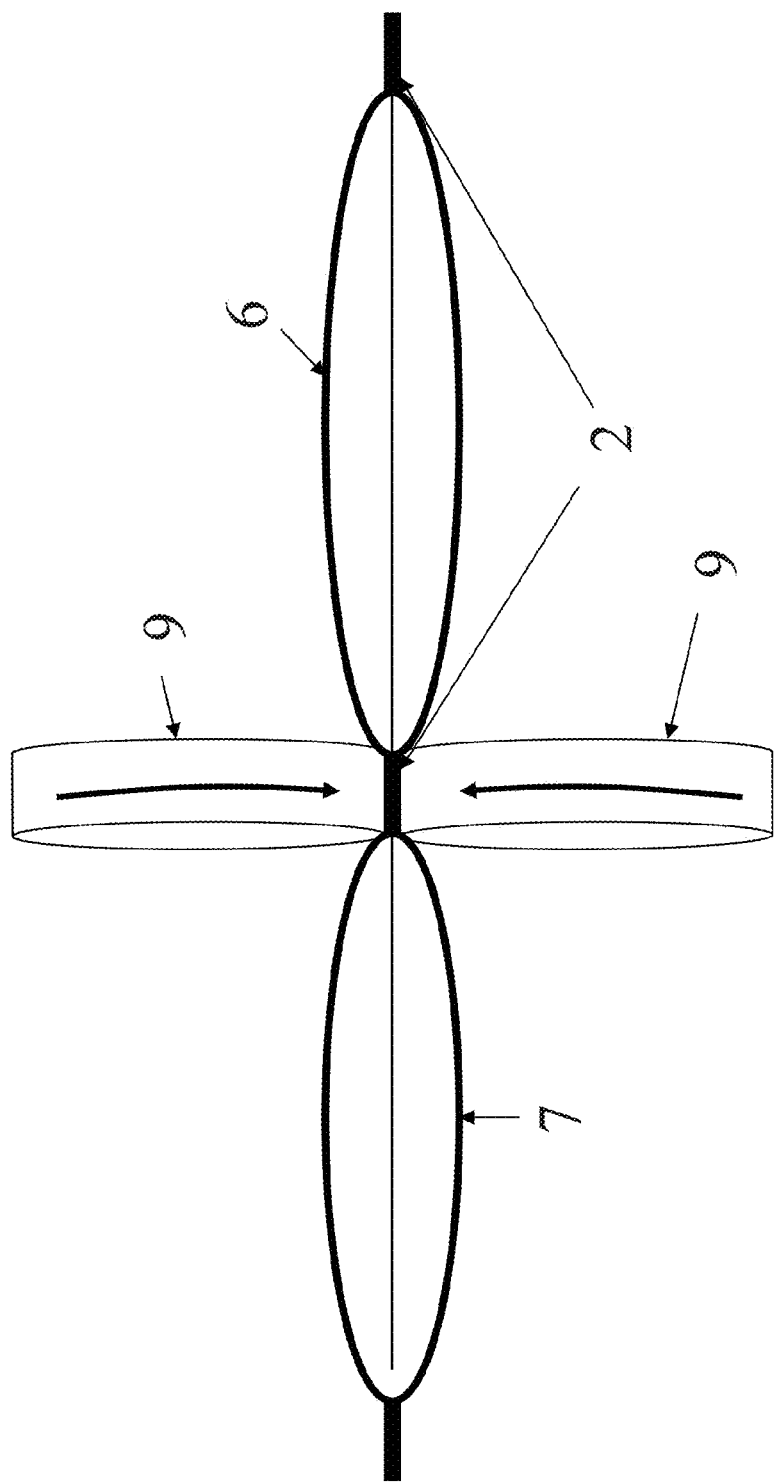
FIG. 4 describes the forming of the configured joints of the PFR by a thermal welding with heated rollers.

There are various methods to create the joint configurations between the two sheets—including but not limited to, thermal and ultrasonic welding and adhesives. An example of the thermal welding approach is displayed in FIG. 4 where the upper film layer 6 is joined to lower film layer 7 by rollers 9. Rollers 9 are positioned on top and bottom of the PFR 1 and may rotate in opposite directions simultaneously along the PFR, exerting heat and pressure along their path thereby forming joints 2.

Recognizing the area-based limit on photon availability, the structure is preferable laid horizontally, or substantially horizontal with a slight incline which may provide free-draining capability for maintenance/replacement. A preferred embodiment of is one of such angle as to provide free-draining within the confines of accuracy of conventional site grading equipment, e.g. 2%.

One facet of the invention is the channel geometry and configuration for optimal light penetration and mixing of the algae broth, while not expending additional material nor incurring large hydraulic pumping costs. The governing parameters and associated ranges of this optimization are broth density (1-12 g/L-affecting maximum depth of light penetration into the channel), lipid production rate (0.5-5 gal/m2/year), channel length as limited by need for nutrient replenishment and oxygen release (<80 m), and flow rate supporting adequate mixing for growth (achieve uniformity of nutrients and lighting) and to reduce the affinity for algae attachment to the film and related fouling (500<Re<5000).

Increasing cell (or broth) density leads to higher efficiency, however, this requires a short light path and/or high mixing rates (dark to light region). Within the reported data, photobioreactors having an optical path <2.6 cm, and highest cell densities, have achieved the highest photosynthetic efficiency (Barbosa). The premise for the present invention is preferable use of turbulent flow (Re>3000) as the control variable. While this in general provides turbulent flow for purposes of general mixing, the diameter of the channel should preferably be limited to within 2.6 cm to achieve mixing times (cell movement from dark to light region) that are preferably less than 15 ms (Barbosa). The requirement for the turbulent flow limit to minimized cell wall fouling may be reduced, however, by alteration of the cell's nature of affinity for attachment and/or the alteration of the film to permit such attachment. The inventor has found that a higher broth density brings about the need for more channels (more wasted and non-productive area in the formation of channel seams) and thus decreases the overall effectiveness. Thus, it is preferred that the channel diameter (or equivalent diameter for non-circular cross sections) be linearly decreasing with the broth density, and the channel count be linearly increasing with broth density. Additionally, for a given reactor length, pumping power increases linearly with broth concentration and the flow rate decreases with increasing broth density.

Figure 5:
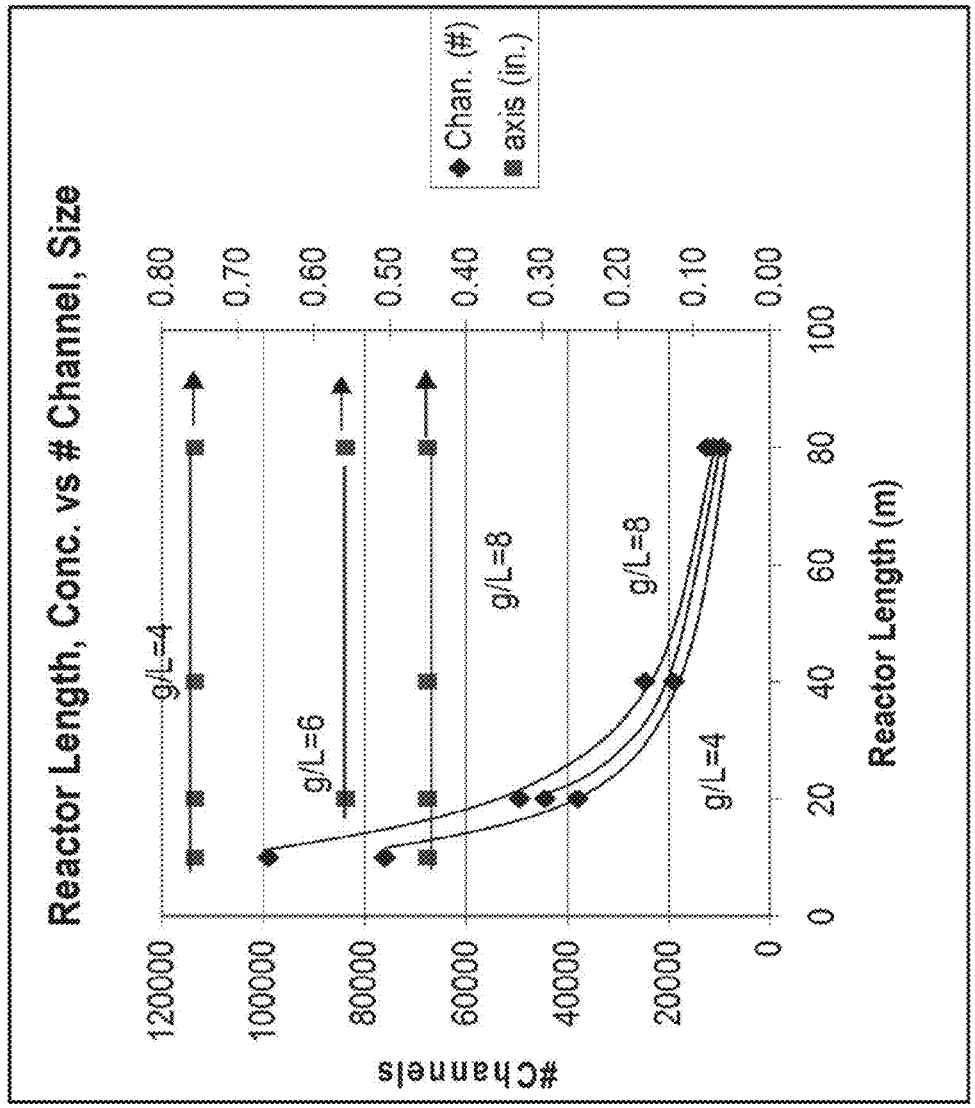
FIG. 5 is a graph describing the effects of varying broth concentration and PFR length on channel count and major axis length.

In general terms, laminar flow exists (0<Re<2000), Transition to turbulent flow is seen (2000<Re<3000), and Turbulent flow (Re>3000).

$$Re = \rho V D / \mu$$

where $\mu$ is the dynamic viscosity
D=pipe diameter
$\rho$=fluid density
V=fluid velocity Once constrained by photobioreactor area, and applying the above criteria, with reference to FIG. 5 channel size and channel count are directly calculated and shown to exhibit parabolic (channel count) and linear (channel axis) relationships with respect to reactor length.

In consideration of cost constraints, material thickness as driven by hydrodynamic pressure, becomes a design factor. For simple tube flow the pressure requiring support by the tube wall is given by:

$$h = \eta (L/D)(\rho * V^2 / 2)$$

where $f$=friction factor

L=pipe Length

The friction factor $f$, varies from a simple linear relationship in the laminar zone ($f$=64/Re), to a more complicated relationship in turbulent flow:

$$1/f = -2.0 \log((\epsilon/D/3.7) + (2.51/Re * f^{0.5})) \quad \text{(Colbrook Equation)}$$

where $\epsilon$ is the equivalent surface roughness.

The stress imposed on the tube wall must be limited to the material strength of the wall. This stress is given by $$\sigma = (h*D)/(2*t)$$

where t is the wall thickness
h is pressure
D is the effective channel diameter

Figure 6:
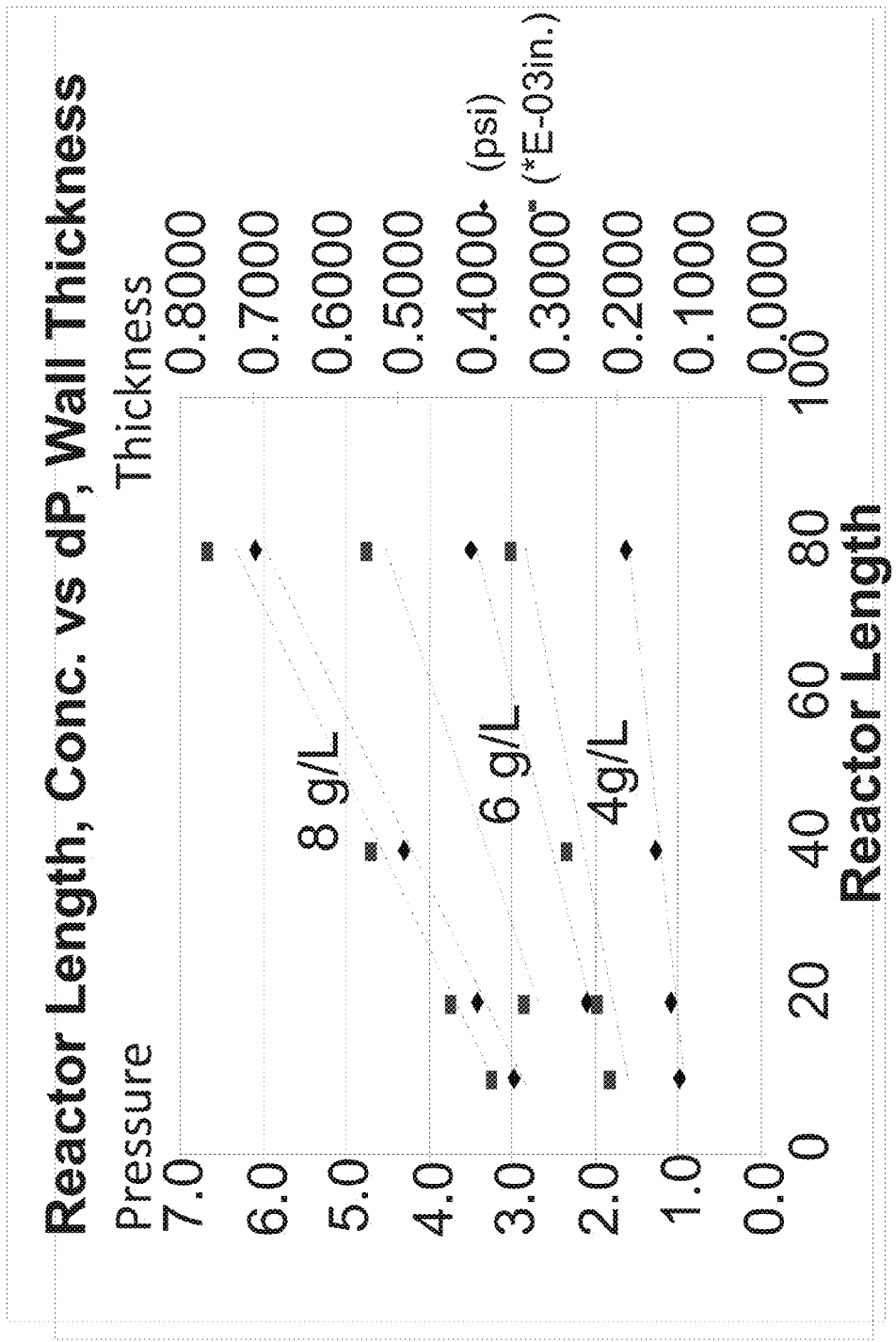
FIG. 6 is a graph describing the effect of varying broth concentration and PFR length on pressure drop and material thickness.

For a film addressing the requisite requirements of high light transmission and low cost, such as low density polyethylene, a relatively low material strength (~1800 psi) is afforded. From the stress relationship, it is seen that wall thickness required increases linearly with pressure and diameter. (FIG. 6).

Over the given range of parameters, the friction loss from straight tube flow places no harsh constraint on the design, i.e. required material thicknesses are beneath 0.001 inch across the range of 0.6 to 6 inch diameter tubes, with Re fixed at 3000. However, entrance and exit losses, and in particular, the use of flow diverting or direction changing features, quickly imparts thickness and cost issues. Pressure loss through direction-altering fittings are given as $$h = K_b * \rho V^2 / 2g$$

where $K_b$ is an experimentally determined factor.

From the inventor's experiments with fittings attached to film tubes, $K_b$ was 54.5. At the conditions of Re=3000, velocity of 0.1 m/s, diameter of 1.761 inches, the observed entrance and exit losses amounted to almost three times that of the straight flow loss. Further experiments with flow diverting and serpentine pattern flows quickly resolved that a straight tube flow was preferable to stay within film thickness requirements as driven by construction and operating cost. Operating cost can be strongly influenced by pump capital equipment and pump energy costs.

The energy requirement is given by:

$$E = Q * h * C$$

Where:
Q=flow rate
h=pressure
C=constant

Figure 7:
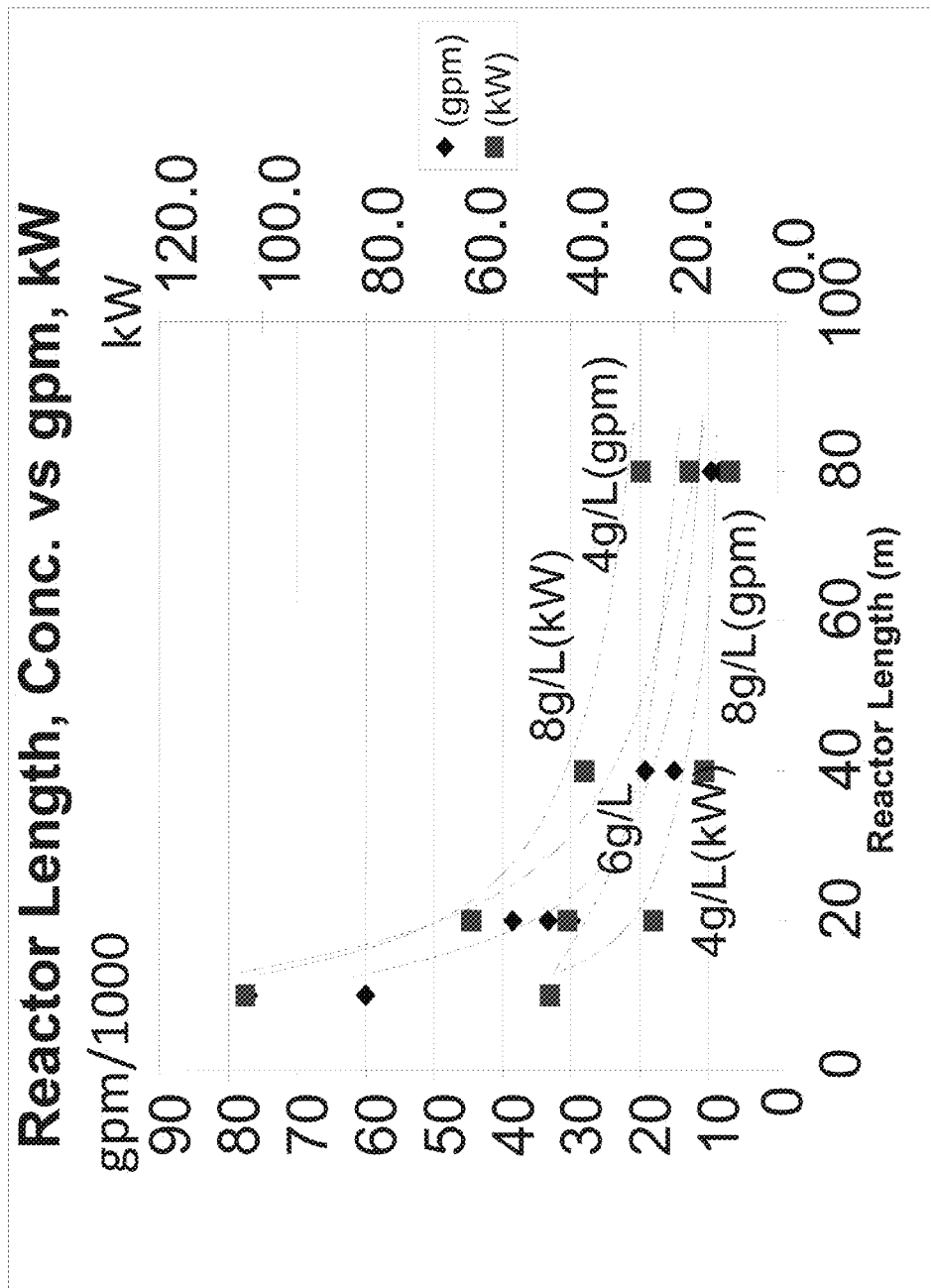
FIG. 7 is a graph describing the effect of varying broth concentration and reactor length on flow rate and pumping power.

Summarized in FIG. 7, total system flow rate (gpm) and required pumping power (KW) exhibit a parabolic relationship with respect to reactor length, per the prior formulation constraints.

Figure 8:
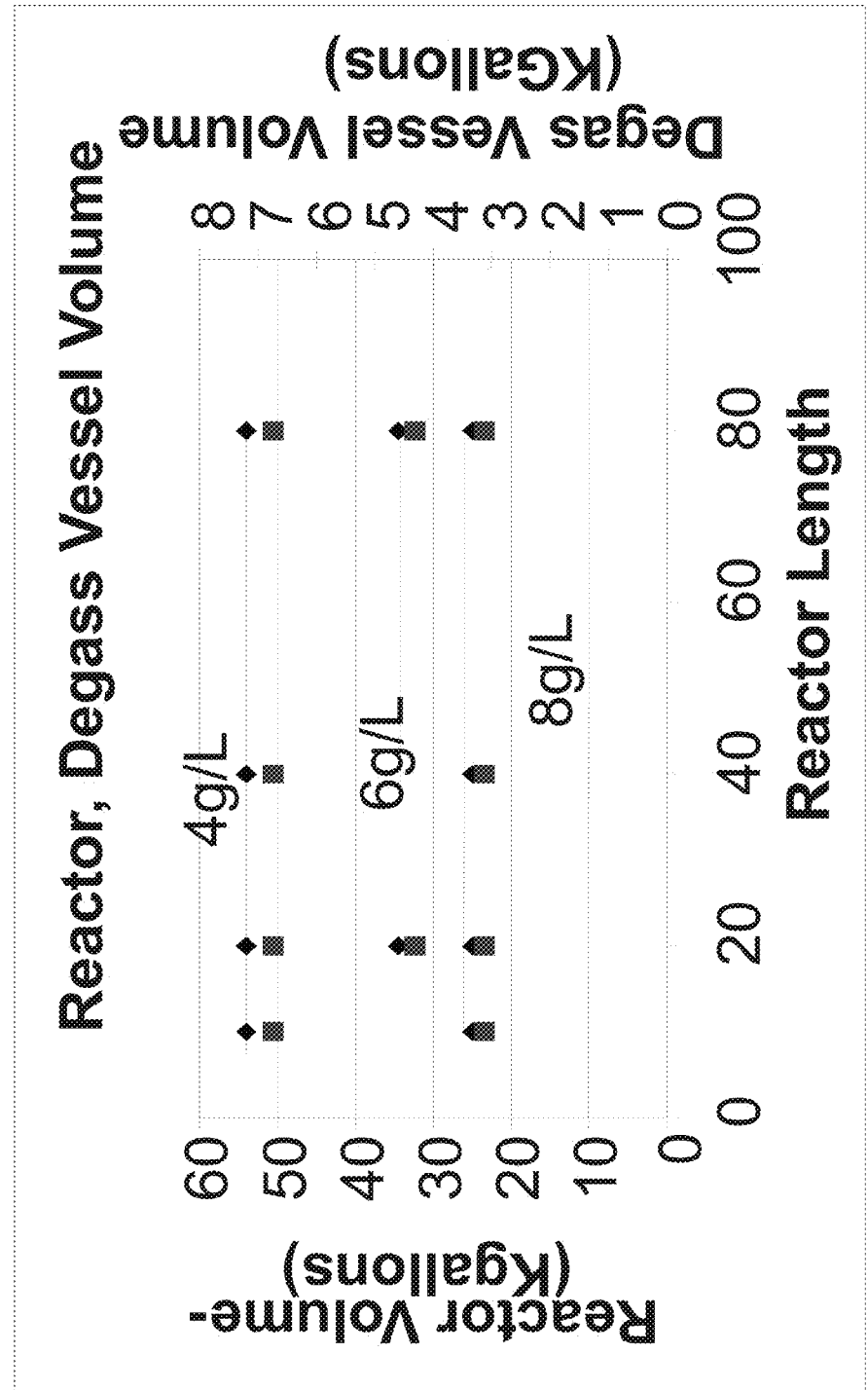
FIG. 8 is a graph describing the effect of varying broth concentration and reactor length on reactor volume and degas vessel size

Another facet of the invention is the constraint to create a scalable unit, optimized for economy-of-scale equipment sizing, and availing design flexibility and reconfigurability. Tank sizing in this analysis can be a driving factor. Typical requirements for the primary degas vessel are ventilation of generated oxygen, and replenishment of nutrients and carbon source (typically carbon dioxide). FIG. 8 reveals the linear relationship of degas vessel volume to reactor length for varying broth densities. Within these requirements, and identification for starting conditions (sufficient volume to initially inoculate the field), the field size is then determined by commercially available plastic tanks which can also be shipped via standard shipping methods (FMCSA limit is 102 inches (2.6 m). This sizing constraint also maintains a relative ease of plant reconfiguration, as well as minimal site preparation (large tanks require significant foundation).

Figure 9:
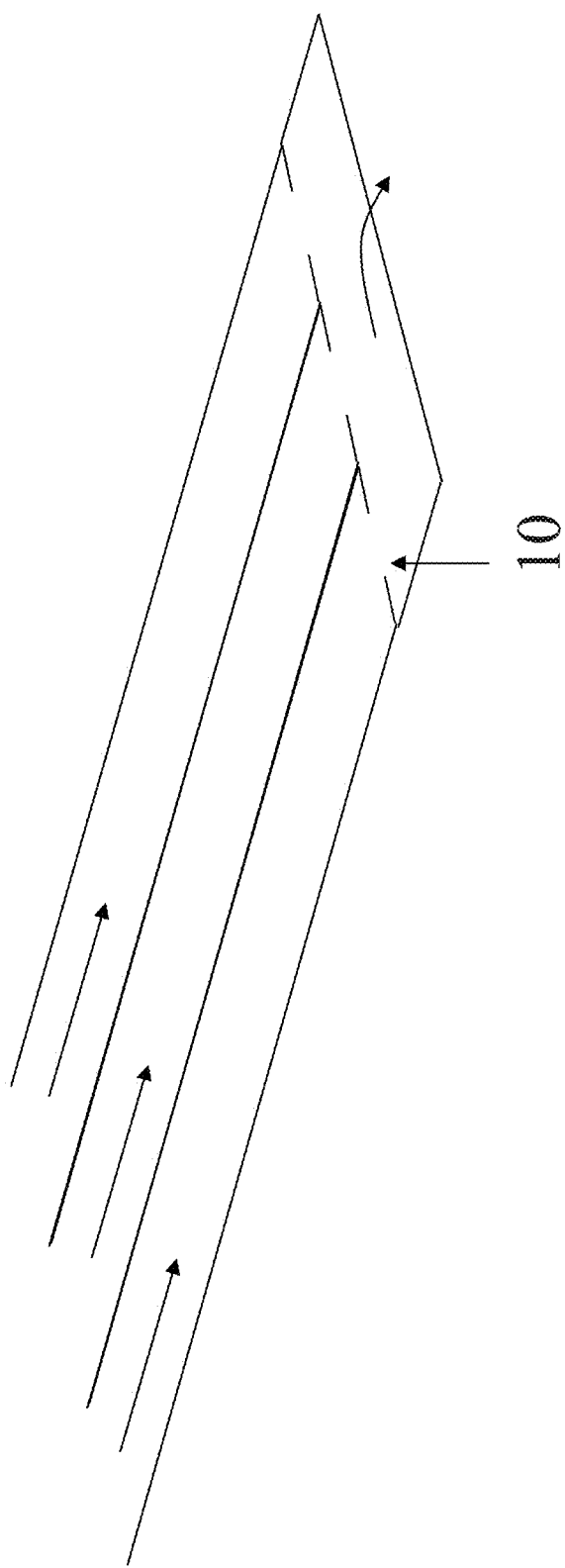
FIG. 9 illustrates the restriction orifice placed at the exit end of a flow channel (entrance to the exit manifold)

A summary analysis using the presented formulation is displayed in FIG. 9. In review of capital equipment cost, pumps, as driven by total system flowrate, are the most significant cost contributor, thus pushing system optimization toward higher broth concentration and higher reactor length.

Example of 80 m, 8 g/L, 3 doublings/day Polyfilm Bioreactor:

Field Size: 5 acres (20,235 m2) (10% availed to non-growth area for access/maintenance)

Oil production: 32,000 gal/year (gross area basis)

Flow characteristics: Re=3000, Ellipse major axis 0.52 inches, 9945 channels (seam-corrected), total flow rate of 7115 gpm Pressure drop: 4.73 psi, requiring material thickness approximately 6.0 mils ("greenhouse film" of 6.0 mils provides adequate strength and may also incorporate UV/IR inhibitors. Using such film the photobioreactor cost is <$3/m2).

Annual Bioreactor Pumping Energy: 68,598 kW-hr (less than $0.12/gal)

Degas Vessel Volume: 3367 gallons

In an alternate configuration, the number/size of pumps may be reduced by one-half by eliminating the return bend at each channel, adding a second and elevated degas vessel at the opposite end of the field. In such configuration, one-half of the bioreactor field channels are pumped via a pump, while the remaining half are pumped via head pressure from the elevated $2^{nd}$ degas vessel. As will be appreciated by those skilled in the art, while this reduces the volumetric flow requirement on the pump(s) by one-half, it increases the pressure requirement on the pump (additional lift up to the elevated vessel), and increases the backpressure on the first half of the bioreactor field channels.

Figure 14:
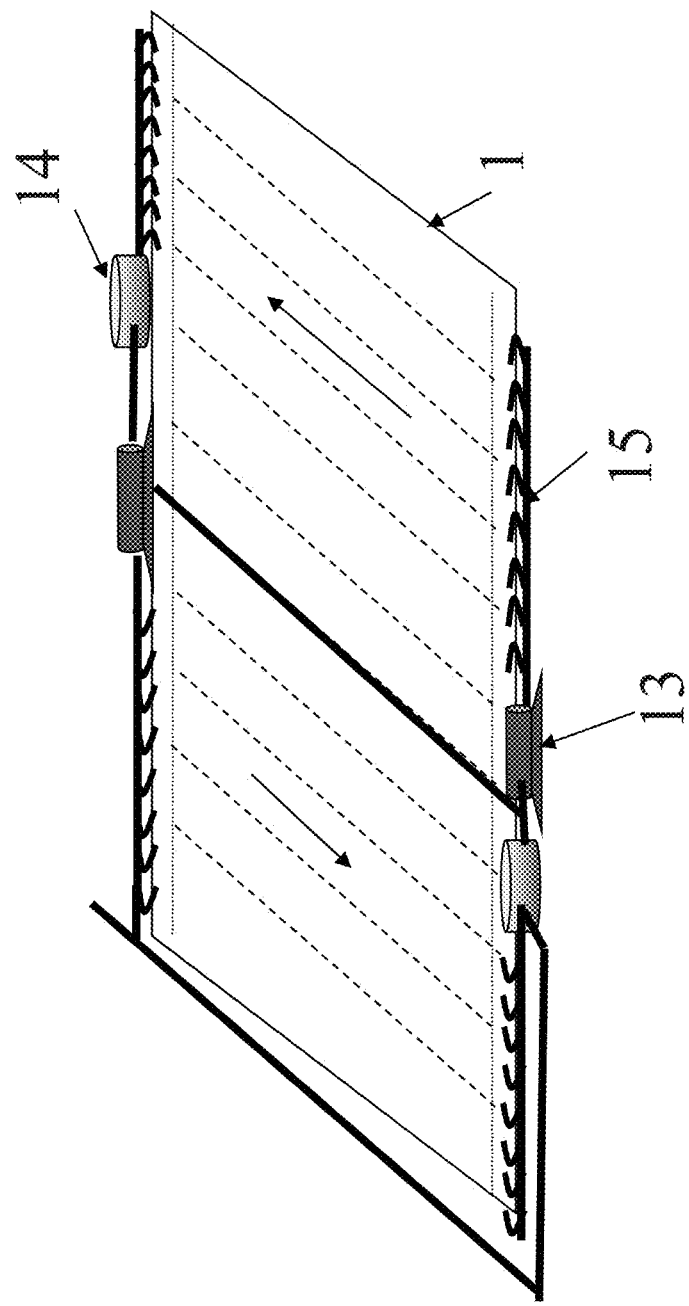
FIG. 14 illustrates a scalable unit showing a pump
Figure 15:
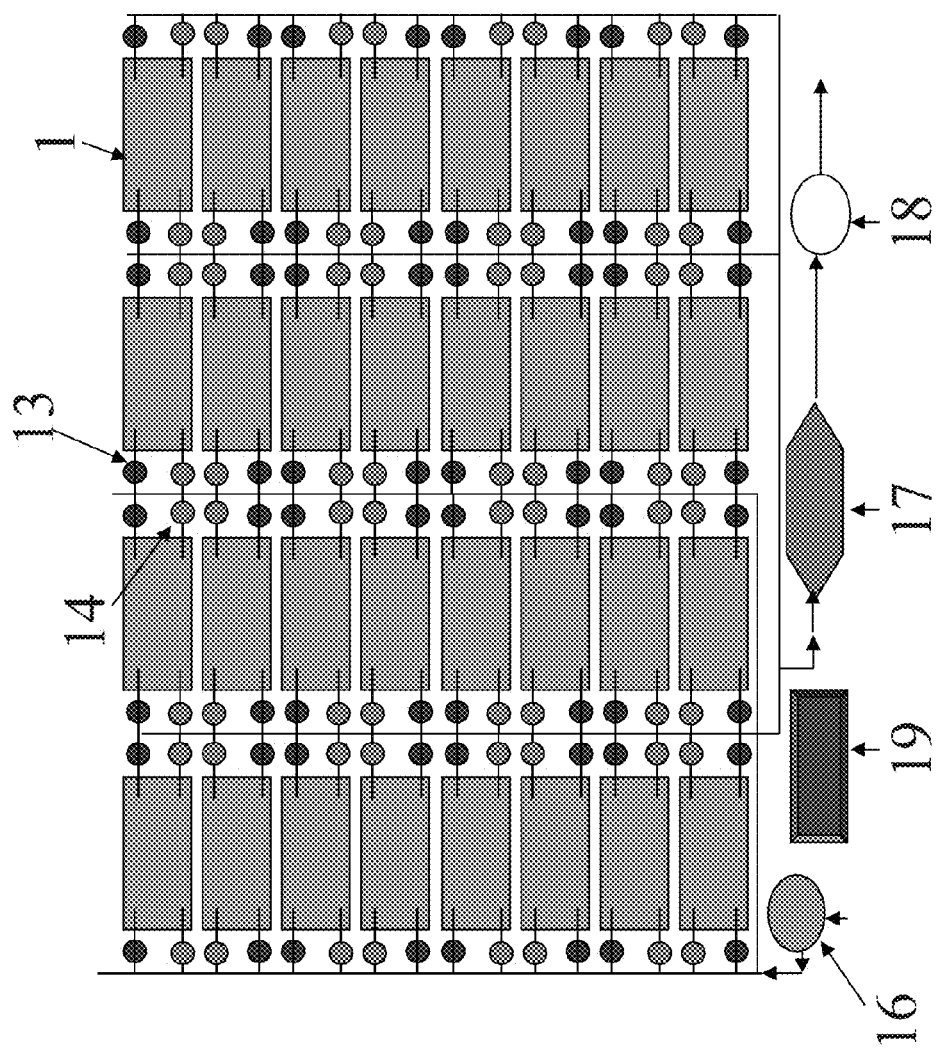
FIG. 15 illustrates the configuration of a scalable unit scaled to 32 units

In one example of the present invention and with reference to FIG. 14, a dual-direction scalable unit is shown using a pump 13 (or alternatively, a plurality of pumps) and a degas vessel 14 (or alternatively, a plurality of vessels) located at opposite ends of PFR unit 1. The pump 13 pumps the algae broth in the direction of arrows 15 which causes flow down the parallel channels 2 before being processed by degas vessel 14. An example of a plant having 32 scalable units sharing common growth media/inoculum supply 16 (station providing an accurated mixture of nutrients, and "starter" algae), control center 19 (station providing for receiving an intelligent and automatic response to sensory information and general process control), extraction facility 17 (wherein lipids and, if desired, by-products, are removed from the algae) and transesterification unit 18 (station in which the lipds are converted from fatty-acids to fatty-acid methyl esters "biodiesel" is shown in FIG. 15.

Another facet of the invention results from examination of the piping and related costs when scaling the design. For example, a 5 acre plant having 1 inch parallel tubes of 80 m length (262 feet), requires the parallel connection of 14,000 tubes. The unit cost of the 28,000 fittings and associated installation easily exceeds the cost target for profitability (not including added maintenance implications). The tube count may be reduced using larger fittings however, the unit fitting cost and installation expense increases with size. The present invention addresses this with a preferred method of manifolding the many channels as a part of the plastic welding configuration. Entrance manifolds 4 and exit manifolds 5 are preferably created by ending the separating welds (or seams) in advance of an extended section of film. This extended section of film is then welded (or seamed) around its periphery, thus completing a pressure-tight manifold. Fluid entrance (or exit) from the manifold can be achieved with a bulkhead type fitting through which the combined flow of the channels is exhausted as shown in FIG. 1.

Given the above stated basis for parallel and manifold flow, another facet of the invention is a requirement for equalizing the flow among the commonly-manifolded channels. In one example of the present invention, sufficient flow and/or equivalence of channel flow resistance is preferably maintained to impart, at a minimum, flow to all channels. In another example of the present invention, flow equivalence can be achieved with the addition of a restriction orifice 10 as shown in FIG. 9, located at the exit end of each channel. Through proper sizing and equivalence of the restrictions, differences in the flow resistance of each channel are insignificant relative to the restrictor resistance, and as this is precisely controlled, so then is the flow equalized. Equalization of flow occurs when the variation in channel resistance is insignificant relative to the orifice pressure drop. For a flat, circular orifice the pressure loss across the orifice is given by:

$$h = Q/(19.63 \cdot K \cdot d^2)$$

where:
h=head in feet
Q=flow in gpm
d=orifice diameter, inches
K=orifice coefficient In an example case of Re=3000, a channel flow rate of 0.7 gallons/minute, an orifice of 0.715 inch diameter will induce a pressure loss of 0.62 psi, or 60% of the channel resistance which one can expect to be in large excess of the variation in channel flow resistance and thus provide equivalence of flow. The constriction orifice may be constructed by inserting an orifice into the channel as a separate member, or it may be constructed by welding a controlled restriction in the channel, averting the cost of an additional component.

Figure 10:
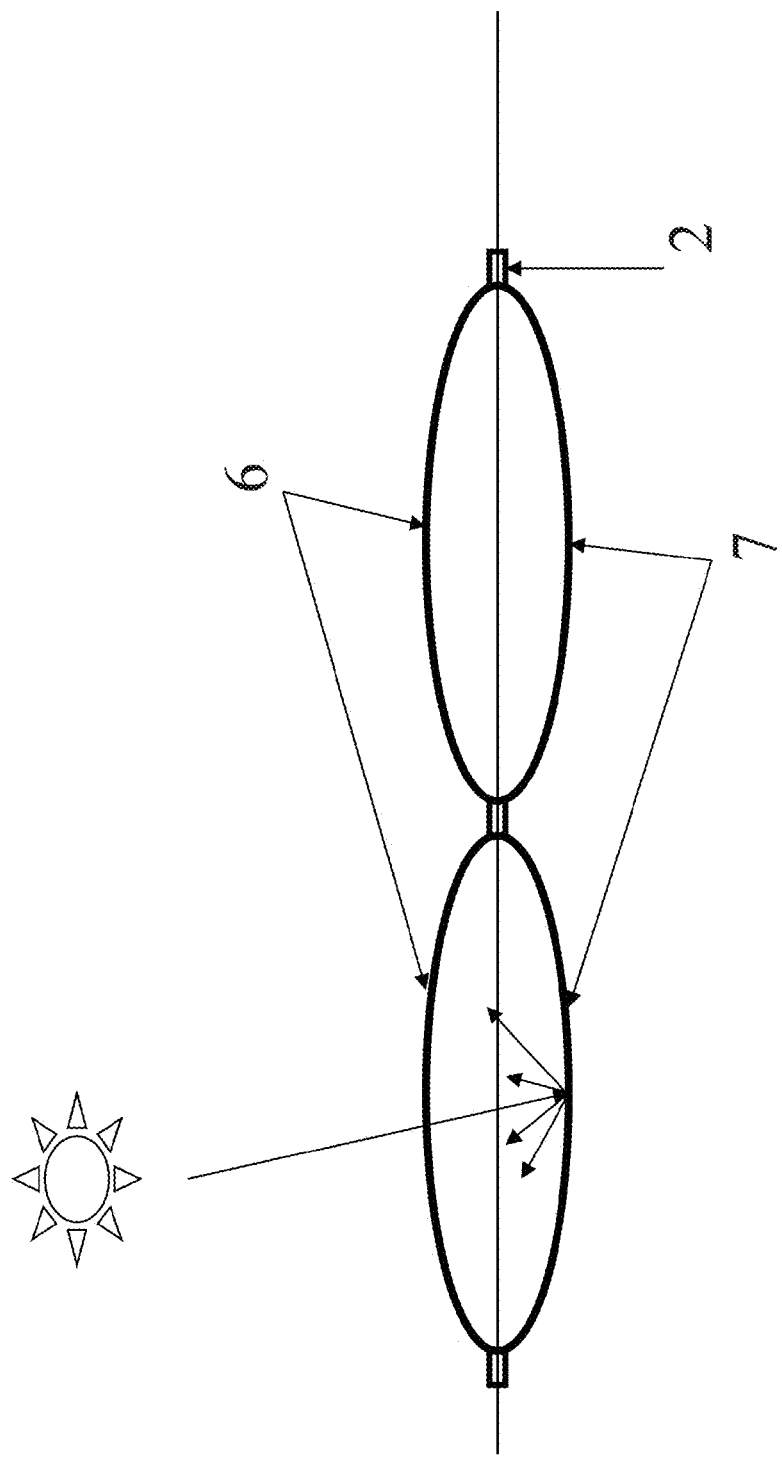
FIG. 10 depicts the cross section of the PFR with the upper film layer of the construction being transparent and the lower layer being a reflective layer.

In an alternative embodiment of the invention and with reference to FIG. 10, the bottom layer 7 of the photobioreactor is made of reflective material thus allowing any light passing through the algae broth to be reflected back into the broth, thereby improving the efficiency of light use in photosynthesis.

Figure 11:
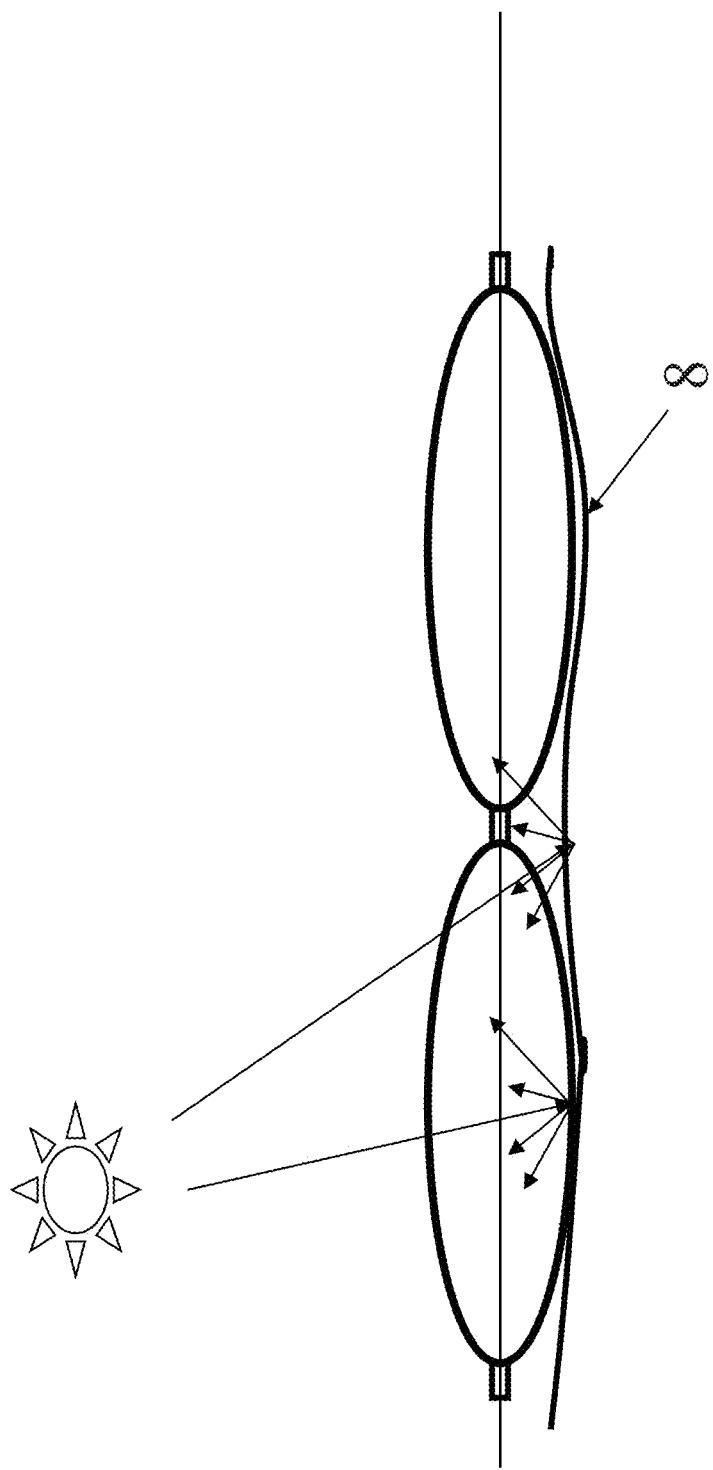
FIG. 11 illustrates the PFR with an underlayer serving as protection, as a reflective surface and/or a plant growth blocking layer.

In another alternative embodiment of the invention and with reference to FIG. 11, an underlay sheet 8 is provided beneath the structure. The underlay sheet 8 may serve as a protection from abrasion or puncture from protruding objects in the surface below, as a reflective layer to reflect any unabsorbed light passing through the photobioreactor back into the photobioreactor, and/or to prevent plant or weed growth beneath the structure.

Figure 12:
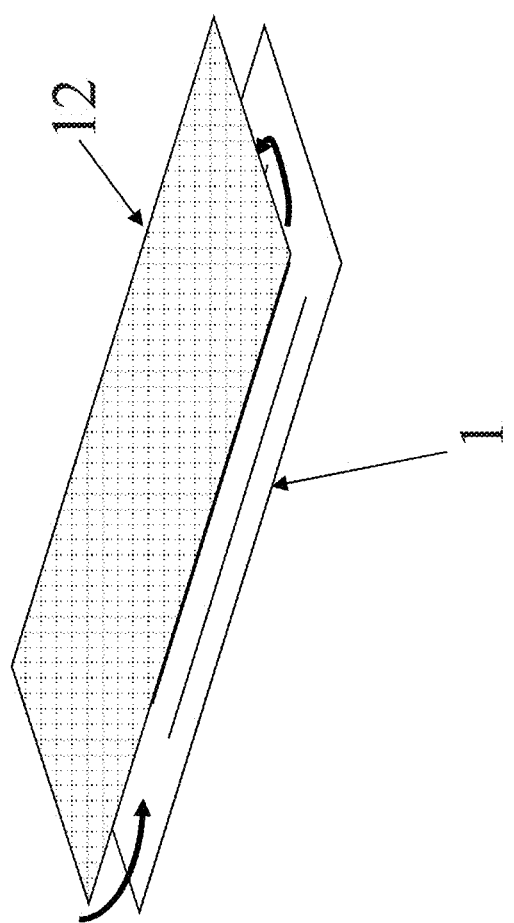
FIG. 12 illustrates the PFR with a mesh-type hail cover

In yet another alternative embodiment of the invention and with reference to FIG. 12, resilience to hail damage is provided by a mesh cover 12 of such strength and opening size as to admit the majority of sunlight, while also being of such strength and having such limitation of opening size to prevent hail damage to the polyfilm photobioreactor. Alternatively, the cover may a simple layer of transparent film.

Figure 13:
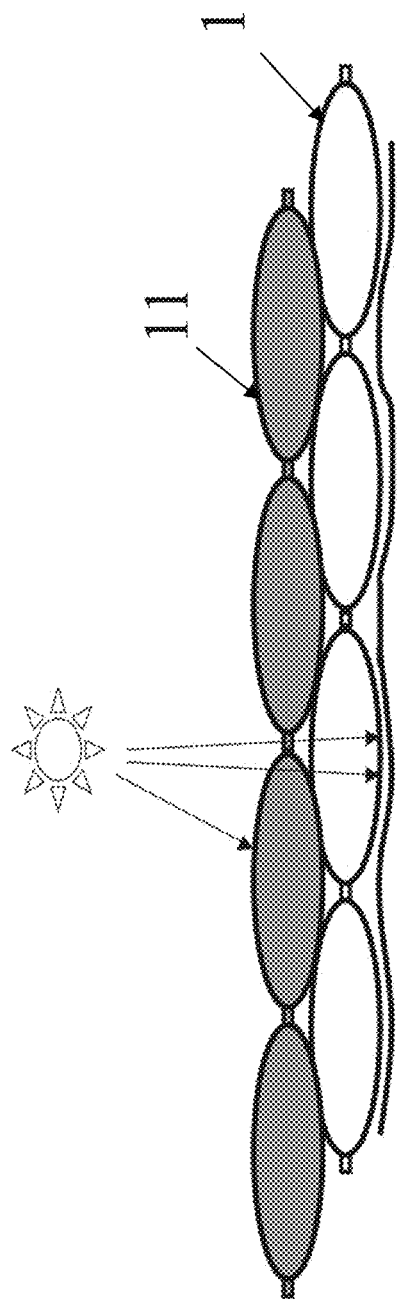
FIG. 13 illustrates a dual-layer PFR which affords redundancy (sacrificial hail layer) and/or availing process variations.

In yet another alternative embodiment of the invention and with reference to FIG. 13 resilience to hail damage is provided by the addition of a second polyfilm photobioreactor 11 over the top of the first layer 1. In such configuration, the channels of the upper layer photobioreactor 11 are preferably interdigitated over the lower photobioreactor 1. The upper layer photobioreactor 11 serves as a sacrificial layer to the lower photobioreactor 1, absorbing hail damage, yet this expenditure does bring return in that more complete capture of the light (seam area light) is enabled. Sensors may be located in the upper photobioreactor 11 to sense failure from a hail or other environmental event, with corresponding control actions to mitigate loss. Additional benefits of such a configuration include use of the upper layer as a shielding during periods of high irradiation (cause for photoinhibition). This upper layer may have the same algae and broth density, be of modulated density (one option being modulated based upon irradiation), or be of a different photosynthetic process entirely (e.g. different algae, cyanobacteria). Further the addition of the second layer affords more heat capacity to the system, thus providing a stabilizing influence over broth temperature through excursions in ambient conditions.

Summarily the present invention provides an economically-viable photobioreactor for biofuels production using transparent film with incorporated parallel flow channels, such channels joined within the film structure forming entrance and exit manifolds. Noted options include the sizing of a scalable unit based upon degas vessel sizing, use of orifices for flow equalization among the channels, and hail damage protection with either a mesh or an upper layer photobioreactor 11. The upper layer photobioreactor 11 presents additional process options, for example, shading of the upper broth over the lower broth, use of differing algaes or photosynthetic processes in upper versus lower.

While the present invention has been described in connection with the various embodiments of the various figures, it is to be understood that other similar embodiments can be used or modifications and additions can be made to the described embodiment for performing the same function of providing the disclosed subject matter without deviating therefrom.

What is claimed:
1. A photobioreactor comprising:
  a. an upper layer of transparent film and a lower layer of film, each of the upper layer and the lower layer substantially parallel with respect to a horizontal plane, wherein the upper layer and the lower layer are attached to each other along the perimeter to form a sealed structure, the upper layer and the lower layer also attached to form parallel flow channels within the confines of the outer perimeter;
  b. a first manifold and second manifold on opposite ends of the parallel flow channels within the sealed structure wherein a first portion of the first manifold is in fluid communication with each of an inlet of a first subset of the parallel flow channels and a second portion of the first manifold is in fluid communication with each of an outlet of a second subset of the parallel flow channels, wherein:
   i. the second manifold is in fluid communications with the distal end of the parallel channels;
   ii. a number and size of channels and a channel diameter are determined based on at least an algae dependent flow variable; and
   iii. the parallel flow channels exhibit a Reynolds number between 500 and 4000;
c. a divider within the sealed structure, wherein the divider separates at least one channel of the parallel flow channels;
d. an orifice at each parallel flow channel within the sealed structure, wherein the orifice facilitates equal flow resistance among the channels; and
e. a plumbing apparatus comprising a degas vessel in fluid communication with the first manifold.

2. The photobioreactor of claim 1 wherein the parallel flow channels are of a serpentine pattern.

3. The photobioreactor of claim 1 wherein the parallel flow channels are parallel and have substantially similar cross-sectional areas under pressure.

4. The photobioreactor of claim 1 further comprising a pump connected to the first manifold.

5. The photobioreactor of claim 1 wherein the lower layer is made of a transparent material.

6. The photobioreactor of claim 1 wherein the lower layer is made of material that reflects light.

7. The photobioreactor of claim 1 wherein the lower layer provides one of abrasion resistance, puncture resistance, a reflective surface, or plant growth resistance.

8. The photobioreactor of claim 1 wherein there is a protective layer positioned above the top layer.

9. The photobioreactor of claim 8 wherein the protective layer is one of a mesh or transparent material.

10. The photobioreactor of claim 1 wherein the parallel flow channels have a cross-sectional area of less than or equal to 6 inches in diameter.

11. The photobioreactor of claim 1 wherein the algae dependent variable comprises a flow channel Reynolds number and a field length as determined by degassing of algae.

12. The photobioreactor of claim 1 wherein the number of parallel flow channels is parabolically decreasing with increasing photobioreactor length.

13. The photobioreactor of claim 1 wherein the channel diameter is linearly decreasing with a broth density, and a channel count is linearly increasing with the broth density.

14. The photobioreactor of claim 1 wherein a pressure drop increases linearly with reactor length and with broth density, thereby giving rise to greater photobioreactor material thickness.

15. The photobioreactor of claim 1 wherein a pumping rate decreases parabolically with respect to reactor length.

16. The photobioreactor of claim 1 wherein a pumping power as determined by a product of flow rate and pressure drop is a parabolically decreasing function with respect to reactor length.

17. The photobioreactor of claim 16 wherein the reactor length is the longest reactor length possible for the given degassing limit and use of a highest broth density.

18. The photobioreactor of claim 1, having a protective cover which is a second photobioreactor laid on top the photobioreactor wherein the channels of each photobioreactor are interdigitated such that the channels of the upper phototbioreactor are positioned the seam areas of the lower photobioreactor, the second photobioreactor providing process options including alternative photosynthetic process and shading options.

19. The photobioreactor of claim 1, wherein the structure is slightly inclined at less than 30 degrees from the horizontal.

* * * * *